(12) United States Patent
Kube et al.

(10) Patent No.: US 11,395,608 B2
(45) Date of Patent: Jul. 26, 2022

(54) MEDICAL SENSOR SYSTEM, IN PARTICULAR CONTINUOUS GLUCOSE MONITORING SYSTEM

(71) Applicant: Roche Diabetes Care, Inc., Indianapolis, IN (US)

(72) Inventors: Oliver Kube, Worms (DE); Helmut Walter, Heppenheim (DE); Alexander Poggenwisch, Colgenstein (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 105 days.

(21) Appl. No.: 16/590,073

(22) Filed: Oct. 1, 2019

(65) Prior Publication Data
US 2020/0046270 A1 Feb. 13, 2020

Related U.S. Application Data

(63) Continuation of application No. PCT/EP2018/058623, filed on Apr. 4, 2018.

(30) Foreign Application Priority Data

Apr. 4, 2017 (EP) .................................... 17164834

(51) Int. Cl.
*A61B 5/145* (2006.01)
*A61B 5/07* (2006.01)
*A61B 5/00* (2006.01)

(52) U.S. Cl.
CPC .......... *A61B 5/14532* (2013.01); *A61B 5/076* (2013.01); *A61B 5/686* (2013.01); *A61B 5/6833* (2013.01); *A61B 2560/0412* (2013.01)

(58) Field of Classification Search
CPC ......... A61B 5/07; A61B 5/076; A61B 5/0031; A61B 5/14532; A61B 5/0024;
(Continued)

(56) References Cited

U.S. PATENT DOCUMENTS 9,259,175 B2    2/2016  Stafford
9,380,698 B1    6/2016  Li et al.
(Continued)

FOREIGN PATENT DOCUMENTS

CN    101528282 A    9/2009
CN    103988238 A    8/2014
(Continued)

OTHER PUBLICATIONS

Darwish, Ashraf; Hassanien, Aboul Ella; Wearable and Implantable Wireless Sensor Network Solutions for Healthcare Monitoring, May 26, 2011, Sensors 2011, 11, 5561-5595 (Year: 2011).*
(Continued)

*Primary Examiner* — Eric F Winakur
*Assistant Examiner* — Alice Ling Zou
(74) *Attorney, Agent, or Firm* — Bose McKinney & Evans LLP

(57) ABSTRACT

A medical sensor system comprising a sensor implantable under the skin of a user and an on-body module attachable to the skin in the region of the implantable sensor, wherein the on-body module has a self-adhering flexible electronics patch including a first transmitter which is operable to exchange data with the implantable sensor via a short-range wireless connection.

18 Claims, 1 Drawing Sheet

(58) Field of Classification Search
CPC ......... A61B 5/0015; A61B 5/024; A61B 5/01; A61B 5/14503; A61B 5/686; A61B 5/6861; A61B 5/6833; A61B 5/002; A61B 5/14546; A61B 5/1459; A61B 5/1473; A61B 5/14865; A61B 5/1451; A61B 5/14735

See application file for complete search history.

(56) References Cited

U.S. PATENT DOCUMENTS

| | | | |
|---|---|---|---|
| 2002/0077673 A1* | 6/2002 | Penner | A61N 1/3787 607/60 |
| 2002/0180605 A1* | 12/2002 | Ozguz | H01L 21/6836 340/573.1 |
| 2008/0119707 A1 | 5/2008 | Stafford | |
| 2008/0161656 A1 | 7/2008 | Bruce et al. | |
| 2008/0275327 A1 | 11/2008 | Faarback et al. | |
| 2009/0076349 A1* | 3/2009 | Libbus | A61B 5/02055 600/301 |
| 2009/0076363 A1* | 3/2009 | Bly | A61N 1/0476 600/372 |
| 2011/0009727 A1 | 1/2011 | Mensinger et al. | |
| 2013/0241745 A1 | 9/2013 | Colvin et al. | |
| 2014/0220422 A1* | 8/2014 | Rogers | H01L 23/08 429/163 |
| 2014/0303452 A1 | 10/2014 | Ghaffari | |
| 2015/0335288 A1* | 11/2015 | Toth | A61B 5/6833 600/373 |
| 2015/0374262 A1 | 12/2015 | Mo et al. | |
| 2016/0006123 A1* | 1/2016 | Li | H01Q 7/00 343/867 |
| 2016/0051735 A1 | 2/2016 | Slepian | |
| 2016/0345874 A1* | 12/2016 | Raisoni | A61M 5/1723 |
| 2017/0055906 A1 | 3/2017 | Bremer | |

FOREIGN PATENT DOCUMENTS

| | | | |
|---|---|---|---|
| CN | 106073798 A | 11/2016 | |
| CN | 106413550 A | 2/2017 | |
| EP | 3 138 489 A1 | 3/2017 | |
| JP | 2010-514536 A | 5/2010 | |
| JP | 2012-135626 A | 7/2012 | |
| JP | 2016-539698 A | 12/2016 | |
| JP | 2017-504446 A | 2/2017 | |
| RU | 126 585 U1 | 4/2013 | |
| WO | WO 2010/056624 A2 | 5/2010 | |
| WO | WO-2010071574 A1 * | 6/2010 | ......... G02B 26/0825 |
| WO | WO-2011084450 A1 * | 7/2011 | ......... H01L 23/3192 |
| WO | WO 2014/096973 A2 | 6/2014 | |

OTHER PUBLICATIONS

Dupont Kapton polyimide film general specification, https://www.dupont.com/content/dam/dupont/amer/us/en/products/ei-transformation/documents/EI-10167-Kapton-General-Specifications.pdf (Year: 2021).*
Dupont Kapton EN polyimide film specification, https://www.dupont.com/content/dam/dupont/amer/us/en/products/ei-transformation/documents/EI-10173-Kapton-EN-Data-Sheet.pdf (Year: 2021).*
International Preliminary Report on Patentability, PCT/EP2018/058623, dated Feb. 4, 2019, 9 pages.
International Search Report and Written Opinion of the International Searching Authority, PCT/EP2018/058623, dated Jun. 28, 2018, 12 pages.

* cited by examiner

MEDICAL SENSOR SYSTEM, IN PARTICULAR CONTINUOUS GLUCOSE MONITORING SYSTEM

RELATED APPLICATIONS

This application is a continuation of PCT/EP2018/058623, filed Apr. 4, 2018, which claims priority to EP 17 164 834.8, filed Apr. 4, 2017, the entire disclosures of each of which are hereby incorporated herein by reference.

BACKGROUND

This disclosure relates to a medical sensor system, in particular to a continuous glucose monitoring system, comprising a sensor implantable under the skin of a user and an on-body module attachable to the skin in the region of the implantable sensor.

Such systems are available for monitoring of certain analytes or agents, specifically glucose or lactate in body fluids like blood or interstitial fluid by readings of a fully or partially implanted sensor, specifically an electrochemical sensor. The subcutaneously implanted sensor remains in the interstitial tissue over an extended period of time even up to several weeks. Then, the in vivo detected measurement signals may be indicative of an analyte, e.g., glucose in the blood of the subject. The monitoring may be a nearly real-time continuous or quasi continuous or periodic approach for frequently providing/updating analyte values without sample handling or similar user interaction.

In present practice, continuous glucose monitoring (CGM)-systems include a so-called bodymount as a patch which has a rigid housing portion or mounting platform on which the electronics unit is mounted and galvanically coupled to the sensor. As the human body is relatively soft and flexible, the rigid housing or platform in connection with the sensor cannot follow the deflections and elongations, thereby resulting in shearing forces which lead to early detachment of the bodymount from the skin. Furthermore, the platform on the body has only reduced breathability, such that humidity accumulates therebelow, which also undesirably reduces the possible wearing time. As a further problem, the open channel through the skin may cause inflammation and body infections.

WO 2010/056624 A2 describes an analyte sensing device having one or more indicating electrodes adapted for long-term use within an individual. An indicating electrode coupled with a reference electrode may be inserted within or below the dermis of an individual and may be electrically coupled to an external sensor unit.

U.S. Publication No. 2008/161656 A1 describes a device, system, and method for delivering a device such as a sensor or fluid transport structure or a fluid transport structure sensor combination into, for example, mammalian skin and receiving, analyzing, and displaying signals from the device such as a sensor. A system includes a reusable sensor assembly including a transmitter, microcontroller, and housing plus disposable sensor assembly including a housing having an opening for receiving both the distal end of a biosensor, a sensor insertion guidance structure, and a transmission apparatus for transmitting signals received from the sensor to a reusable sensor assembly for transmission to an external electronic monitoring unit.

U.S. Publication No. 2011/009727 A1 describes systems and methods for continuous measurement of an analyte in a host. The system generally includes a continuous analyte sensor configured to continuously measure a concentration of analyte in a host and a sensor electronics module physically connected to the continuous analyte sensor during sensor use, wherein the sensor electronics module is further configured to directly wirelessly communicate displayable sensor information to a plurality of different types of display devices.

U.S. Publication No. 2017/055906 A1 describes optical sensors, systems and methods for continuous glucose monitoring. In some embodiments, methods of preparing a layered optical sensor are disclosed. The optical sensor can be formed by laminating a plurality of sheets together to form a final sensor. In some embodiments, the sensor tip comprises an oxygen conduit, an enzymatic layer, and a sensing layer. In some embodiments, the sensor includes a plurality of waveguides configured to direct light to and from a target material, such as an oxygen sensing polymer. Systems are also disclosed for an adhesive system for attaching an optical sensor-transmitter system. Methods and systems are also disclosed for a sensor inserter system. The inserter can include a lancet tip that includes a convex feature attached to a first surface of the lancet tip.

U. S. Publication No. 2016/051735 A1 describes methods, materials, devices, and systems for electropolymeric paving and sealing (ePEPS). The methods include delivering paving materials to an interior surface of a blood vessel, tissue lumen or other hollow space, delivering electronic components to the surface, and forming a conformal device that contains the paving material and the integrated electronic components. Integrated electronic components can be homogenously or heterogeneously distributed in the material, such as on the top, middle, and/or bottom of the polymeric material. The devices are biocompatible, and preferably biodegradable or bioerodible. The devices have integrated electrical properties useful for sensing or detecting one or more analytes, signals or conditions, transmitting or generating a signal, or releasing a therapeutic, prophylactic or diagnostic agent. Optionally, the devices are smart devices that include feedback and logic means to respond to a change in local conditions.

EP 3 138 489 A1 describes a kit for determining a concentration of at least one analyte in a body fluid of a user. The kit comprising: a) a sensor module comprising i. at least one sensor element adapted to determine the concentration of the analyte, wherein the sensor element is at least partly implantable into a body tissue of the user; ii. at least one control device connected to the sensor element, wherein the control device comprises at least one data collection device adapted to collect measurement data acquired by using the sensor element, wherein the control device further comprises at least one wireless near-field communication device adapted to transmit measurement data, wherein the sensor module comprises a sensor module mechanical interface; b) at least one data reader module adapted to receive measurement data transmitted by the sensor module via wireless near-field communication, wherein the data reader module comprises at least one data storage device and is adapted to store the measurement data; c) at least one data transmission module adapted to receive measurement data transmitted by the sensor module via wireless near-field communication, wherein the data transmission module comprises at least one wireless far-field communication device, wherein the wireless far-field communication device is adapted to transmit at least part of the measurement data to an external device via wireless far-field communication. The data reader module and the data transmission module each comprise a mechanical interface adapted to reversibly engage the sensor module mechanical interface, thereby alternatively generating a fixed spatial relationship between the sensor module and the data reader module or the sensor module and the data transmission module.

SUMMARY

On this basis, this disclosure further improves the known systems and provides a design which allows for long-term wear capability and wear comfort.

This disclosure is based on the idea of physically separating the sensor from a flat on-body module. Accordingly, it is proposed that the on-body module has a self-adhering flexible electronics patch only including a first transmitter which is operable to exchange data with the separated implantable sensor via a short-range wireless connection. As used herein, the term "including a first transmitter" refers to an embodiment in which the electronics patch comprises only the first transmitter and to embodiments in which the electronics patch comprises additional components, in particular additional electronics components, as will be outlined below. As used herein the term "patch" refers to at least one arbitrary shaped fastening element which is configured to be attached directly to the skin of the user, i.e., without using additional or further fastening elements. As used herein, the term "self-adhering" refers to the patch comprising at least one attachment side, for example a bottom side, adapted to attach and/or mount the patch to the skin, wherein the attachment side comprises at least one adhesive and/or is coated with at least one adhesive coating. As used herein, the term "electronics patch" refers to a patch which comprises at least one electronic element. As used herein, the term "flexible electronics patch" refers to the fact that the electronics patch has flexible properties such that the electronics patch is bendable and/or stretchable to follow the contour of the skin. The patch may have a stretchability of at least 20% in at least two directions, preferably in all directions. As used herein "stretchability of at least 20%" refers to that a patch having a length of, for example, 10 cm (centimeters) can be stretched to a length of at least 12 cm (centimeters). The flexible patch avoids the disadvantages of a rigid platform and, at the same time, allows for data exchange through the skin, while the sensor is kept aseptic and needs not be replaced together with the patch. Thus, the overall operating cycle can be prolonged and the user convenience can be significantly improved.

The medical sensor system comprises the on-body module attachable to the skin in the region of the implantable sensor. As used herein, the term "attachable to the skin in the region of the implantable sensor" refers to that the electronics patch and the implantable sensor are physically separated, in particular spatially separated. Specifically, the electronics patch and the implantable sensor are not physically connected. For example, the distance between the implantable sensor and the electronics patch may be in the range from 3 to 10 mm.

In an advantageous embodiment, the flexible electronics patch comprises flexible printed circuits (FPC) provided on an insulating foil substrate, e.g., on a thin polymer film, such that the patch is bendable and/or stretchable to follow the contour of the skin.

The foil having the printed circuits thereon may be a polyimide foil carrying a structure which is galvanically printed. Preferably the foil is a stretchable, breathable foil and the structure is printed with conductive ink (including, e.g., silver and/or carbon particles).

Advantageously, the foil substrate is stretchable in at least one direction by more than 20% of its initial length. In an embodiment the foil substrate may be stretchable in at least two directions by more than 20%. In an embodiment the foil substrate is stretchable in all directions by more than 20%. As used herein the term "more than 20%" in an embodiment means that a foil substrate having a length of, for example 10 cm (centimeters), can be stretched along its length to at least 12 cm (centimeters).

Preferably, the insulating foil substrate has a thickness in the range of 10 to 250 microns, preferably 50 to 100 microns, more preferably 60 to 90 microns and most preferably 70 to 80 microns. Depending on the stability of the foil, a thickness in the range of 10 to 50 microns might also be feasible.

The electronics patch may comprise at least one deformable electronics element and/or at least one rigid or semi-rigid electronics element. For example, the electronics patch may comprise at least one flexible printed circuitry including at least one electronic element selected from the group consisting of: at least one conductive path, at least one resistor, at least one capacitor, and at least one battery, wherein the electronic elements may be deformable components. For example, the electronics patch may comprise rigid or semi-rigid components such as one or more of at least one integrated circuit chip, at least one processor, at least one storage medium, at least one antenna, and at least one battery. As used herein, the term "comprises at least one deformable electronics element and/or at least one rigid or semi-rigid electronics element" refers to that the deformable electronics element and/or the rigid or semi-rigid electronics element is part of the patch and/or is integrated within or into the patch, in particular is integrated within at least one substrate of the patch and/or on at least one substrate of the patch and/or is integrated within at least one layer of the patch, and/or that the deformable electronics element and/or the rigid or semi-rigid electronics element is embedded within the patch and/or that the deformable electronics element and/or the rigid or semi-rigid electronics element is incorporated in the patch. For example, the patch may comprise the insulating foil substrate having the deformable electronics element and/or the rigid or semi-rigid electronics element printed thereon, in particular directly. Specifically, the deformable electronics element and/or the rigid or semi-rigid electronics element may be integrated and/or incorporated and/or embedded in the patch such that the patch itself is arranged and/or configured as an electronic unit. Thus, the deformable electronics element and/or the rigid or semi-rigid electronics element may be comprised by the patch itself, without the need of an additional and/or separate element adapted to store or house the deformable electronics element and/or the rigid or semi-rigid electronics element such as a housing or base unit or something similar.

For providing a flat flexible assembly, it is preferred that the flexible printed circuits include at least one of conductive paths, resistors, capacitors and batteries formed as deformable components. It may also be conceivable that even processors and other ICs, antennas for communication and storage media are integrated as flexible components, which would lead to a fully flexible FPC.

Another possibility provides that the flexible electronics patch comprises at least one of integrated circuit chips, processors, storage media, antennas and batteries as rigid or semi-rigid components which are distributed such that the electronics patch overall remains deformable to adapt its shape to a varying contour of the skin during use.

Advantageously, the short-range wireless connection is established via a pair of antennas which are coupled by electromagnetic induction and preferably work in the radio frequency range. Such an antenna arrangement can be easily realized in a flat configuration on a flexible substrate.

A particular embodiment further comprises that the data exchange is based on near-field communication (NFC) protocol. This allows for reliable wireless connection in the required range varying from a few millimeters up to 2 centimeters. The range for near-field communication may be from 3 to 10 mm. The data transmission could even be provided unencrypted without safety concerns since the transmission is only effected over small distances.

In an advantageous embodiment, the first transmitter is operable to receive measured values from the sensor and eventually to transmit calibration data to the sensor. In the latter case, the measurement accuracy can be maintained even when sensor characteristics are changing. It is also conceivable that calibration in use may not be required if the system is factory calibrated.

In another advantageous configuration, the on-body module further comprises a patch-mounted energy supply configured to supply the sensor with energy by contactless transmission. Preferably, inductive energy transmission is provided to load a capacitor on the implanted sensor. Thus, a battery needs not to be integrated in the sensor. Such an arrangement is also more safe for the patient. Furthermore, electrical power supply can be maintained over a long period.

Advantageously, the flexible electronics patch comprises a printed battery which consists of functional materials, e.g., a zinc manganese dioxide system, printed on a flexible substrate. Other commercially available systems may also be feasible.

A fully flexible battery may be arranged above or below the FPC in a layered configuration. Depending on the arrangement of the flexible battery (which may include a metallic foil), the antenna arrangement needs to be placed such that it is not shielded by the battery. In specific configurations, multiple antennas may be used above and below the printed battery, or on the side thereof.

In still another advantageous configuration, the on-body module further comprises a second transmitter integrated with the patch and operable for wireless data exchange with an external data acquisition device positioned in a far-field region. In this arrangement, data exchange via bluetooth low energy communication protocol is preferred. Preferably, such a device is configured as a handheld and operated at a distance of at most a few meters from the patch.

In order to realize a closed loop system, a body-mounted pump may be provided as a separate physical entity to deliver doses of a medical agent such as insulin to the body of the user in response to a measuring result achieved with the sensor.

In this connection it is further advantageous when the on-body module comprises at least one of a controller, a switch and a display, specifically a pressure-sensitive display, directly attached to the flexible patch for allowing the user to operate the system without remote control.

In another advantageous embodiment, the system comprises a plurality of sensors distributed in a body area and connected in a network to the on-body module. This allows for mutual control and monitoring of different influencing parameters. In such a network, data from all sensors are communicated to the on-body module, which is then a master in the system. Alternatively, any other of the separate sensor components may be the master. All sensors may be realized in the form of flexible patches comprising flexible electronics. The data from these sensors may be communicated to a remote control, preferably by a bluetooth low energy (BLE) connection, via the master. There, the data may be further processed to gain more insight into the patient's glycemic status.

Preferably, the plurality of sensors is adapted to measure at least one parameter selected from the group: glucose, temperature, body movement, tremor, heart rate, perspiration.

In a further aspect a method for continuous monitoring of at least one analyte in at least one body fluid is proposed. The method comprises the following steps which, as an example, may be performed in the given order. It shall be noted, however, that a different order is also possible. Further, it is also possible to perform one or more of the method steps once or repeatedly. Further, it is possible to perform two or more of the method steps simultaneously or in a timely overlapping fashion. The method may comprise further method steps which are not listed. The method comprises using at least one medical sensor system according to any one of the embodiments as described above or described in detail below. The method comprises the following steps:

i) attaching an on-body module to the skin of the user in the region of a sensor implanted under the skin of a user using a self-adhering flexible electronics patch, wherein the self-adhering flexible electronics patch includes a first transmitter;

ii) exchanging data between the first transmitter of the self-adhering flexible electronics patch with the implantable sensor via a short-range wireless connection.

With respect to embodiments and definition of the method reference is made to the description of the medical system above and as described in further detail below.

Summarizing and without excluding further possible embodiments, the following embodiments may be envisaged:

Embodiment 1

Medical sensor system, in particular continuous glucose monitoring system, comprising a sensor implantable under the skin of a user and an on-body module attachable to the skin in the region of the implantable sensor, wherein the on-body module has a self-adhering flexible electronics patch including a first transmitter which is operable to exchange data with the implantable sensor via a short-range wireless connection.

Embodiment 2

The system of embodiment 1, wherein the flexible electronics patch comprises flexible printed circuits provided on an insulating foil substrate.

Embodiment 3

The system of embodiment 2, wherein the insulating foil substrate has a thickness in the range of 10-250 microns, preferably 50-100 microns, more preferably 60-90 microns and most preferably 70-80 microns.

Embodiment 4

The system of embodiment 2 or 3, wherein the flexible printed circuits include at least one of conductive paths, resistors, capacitors and batteries as deformable components.

Embodiment 5

The system according to any of embodiments 1 to 4, wherein the flexible electronics patch comprises at least one of integrated circuit chips, processors, storage media, antennas and batteries as rigid or semi-rigid components which are distributed such that the electronics patch remains deformable.

Embodiment 6

The system according to any of embodiments 1 to 5, wherein the short-range wireless connection is established via a pair of antennas which are coupled by electromagnetic induction.

Embodiment 7

The system according to any of embodiments 1 to 6, wherein the data exchange is based on near-field communication (NFC) protocol.

Embodiment 8

The system according to any of embodiments 1 to 7, wherein first transmitter is operable to receive measured values from the sensor and eventually to transmit calibration data to the sensor.

Embodiment 9

The system according to any of embodiments 1 to 8, wherein the on-body module further comprises a patch-mounted energy supply configured to supply the sensor with energy by contactless transmission.

Embodiment 10

The system according to any of embodiments 1 to 9, wherein the flexible electronics patch comprises a printed battery which consists of functional material printed on a flexible substrate.

Embodiment 11

The system according to any of embodiments 1 to 10, wherein the on-body module further comprises a second transmitter integrated with the patch and operable for wireless data exchange with an external data acquisition device positioned in a far-field region.

Embodiment 12

The system according to any of embodiments 1 to 11, further comprising a body-mounted pump to deliver doses of a medical agent such as insulin to the body of the user in response to a measuring result achieved with the sensor.

Embodiment 13

The system according to any of embodiments 1 to 12, wherein the on-body module comprises at least one of controller, switches and display directly attached to the flexible patch for allowing the user to operate the system without remote control.

Embodiment 14

The system according to any of embodiments 1 to 13, further comprising a plurality of sensors distributed in a body area and connected in a network to the on-body module.

Embodiment 15

The system of embodiment 14, wherein the plurality of sensors are adapted to measure at least one parameter selected from the group: glucose, temperature, body movement, tremor, heart rate, perspiration.

Embodiment 16

A method for continuous monitoring of at least one analyte in at least one body fluid, wherein the method comprises using at least one medical sensor system according to any one of the preceding embodiments, wherein the method comprises the following steps:
  i) attaching an on-body module to the skin of the user in the region of a sensor implanted under the skin of a user using a self-adhering flexible electronics patch, wherein the self-adhering flexible electronics patch includes a first transmitter;
  ii) exchanging data between the first transmitter of self-adhering flexible electronics patch with the implantable sensor via a short-range wireless connection.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
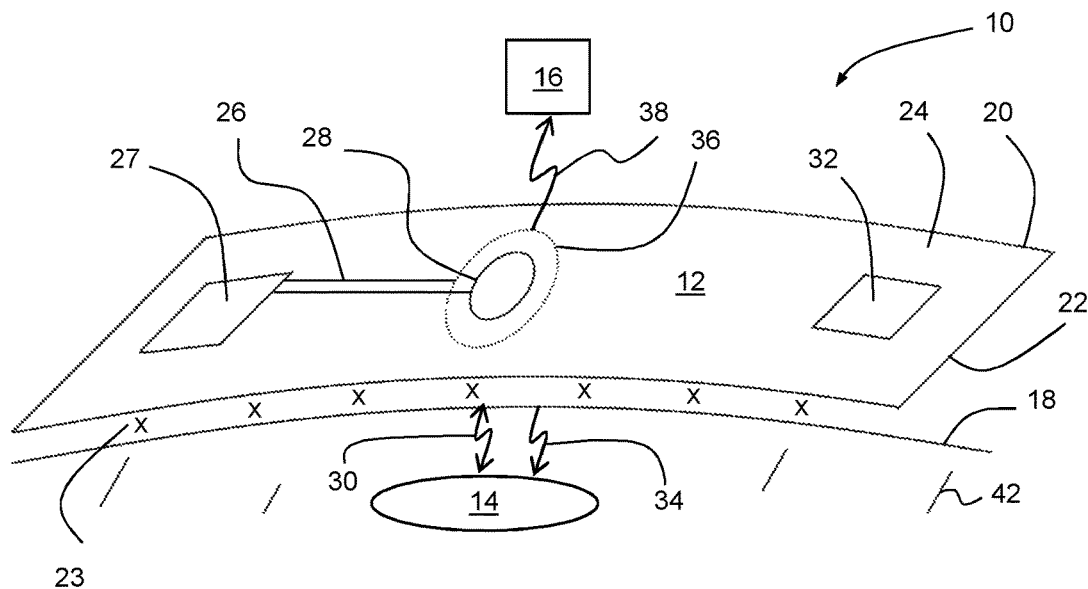
FIG. 1 is a sectional and partially 3D-expanded view of a medical sensor system including a body-mountable flexible patch and a skin-implanted sensor interconnected by wireless connections.

Referring to FIG. 1, a medical sensor system 10 for continuous analyte monitoring in a body fluid, specifically continuous glucose monitoring, comprises at least one on-body module 12, a fully subcutaneously implanted glucose sensor 14 which is completely arranged in the subcutaneous tissue below the skin, and optionally a handheld data acquisition device 16 for receiving information from the module 12.

The module 12 is attachable to the skin 18 of the user in the region of the implanted sensor 14. For this purpose, the module 12 comprises a self-adhering planar electronics patch 20 based on a flexible foil material 22. The electronics patch 20 has a bottom side coated with an adhesive 23 to attach the patch 20 to the user's skin 18 and a top side 24 facing away from the skin for carrying flexible printed circuits and conducting pathways 26 and eventually rigid or semi-rigid electronic components 27 directly mounted on the patch foil 22.

A first transmitter 28 mounted on the electronics patch 20 is operable to exchange data with the implantable sensor 14 via a short-range wireless connection 30. Such a connection may be established via antennas on the side of the patch 20 and of the sensor 14 which are coupled by electromagnetic induction. The data exchange can be based on a near-field communication (NFC) protocol, which is known per se to the skilled person.

In this way, the first transmitter 28 can be operated to transmit calibration data to the sensor 14. In the other direction, the sensor 14 transmits analyte readings and/or other measurement data to the patch 20 for further processing in the electronic components 27.

In order to avoid any galvanic connection through the skin 18, the module 12 further comprises a patch-mounted energy supply 32 configured to supply the sensor 14 with electric energy by contactless transmission through inductive path 34. The energy supply 32 may be realized as a printed battery which consists of functional electrode and electrolyte materials printed on a flexible substrate.

As also apparent from FIG. 1, the on-body module 12 further comprises a second transmitter 36 integrated with the patch 20 and operable for wireless data exchange with the external data acquisition device 16. Here, a transmission path 38 may be provided for far-field communication in the range of at least several meters. The data acquisition device 16 may allow for controlling the module 12 in addition to receiving information from it.

The disposable sensor 14 may include electrodes in contact with the interstitial fluid and providing analyte readings, e.g., based on electrochemical reactions. Specifically, glucose readings may be correlated to blood glucose levels for allowing the user continuous or quasi-continuous in vivo monitoring.

Figure 2:
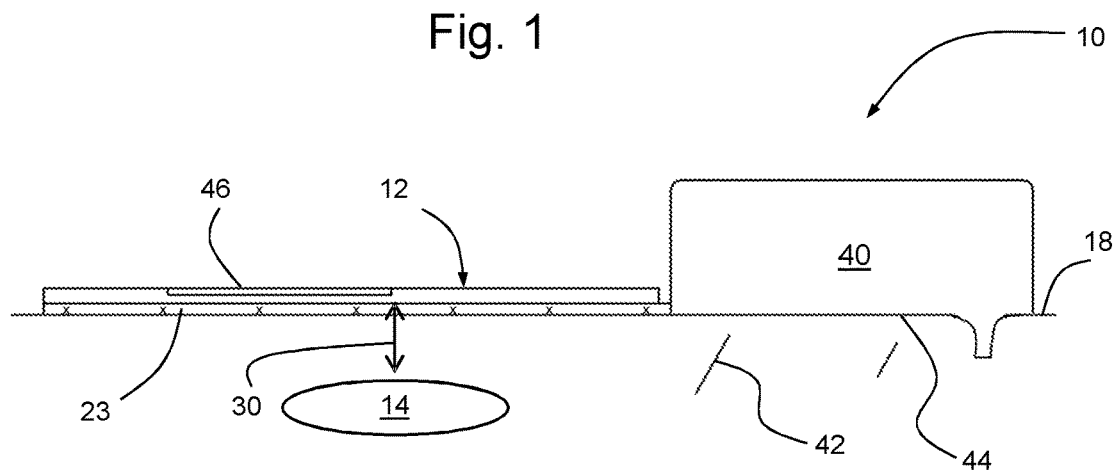
FIG. 2 is a sectional view of another medical sensor assembly similar to FIG. 1 and including a body-worn patch pump.

As further illustrated in FIG. 2, the system 10 can also include a body-mounted pump 40 for delivering doses of a medical agent to the body 42 of the user. The pump 40 can be arranged on an adhesive patch 44 directly on the skin 18. In operation, pump 40 receives control signals from module 12 to supply bolus doses of insulin in response to a measuring result achieved with the sensor 14. For improved convenience, the module 12 comprises a controller 46 including an interface for allowing the user to operate the system 10 without remote control.

Figure 3:
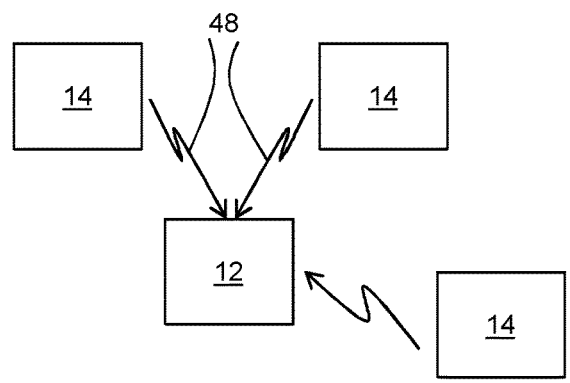
FIG. 3 is a top view of a network of on-body modules including various skin-implanted sensors.

In the embodiment of FIG. 3, a plurality of sensors 14 are distributed in a body area of the user and are connected in a wireless network 48 to the on-body module 12. The sensors 14 are adapted to measure different body parameters, e.g., glucose, body temperature and movement, tremor, heart rate, perspiration. In this network 48, data from all sensors 14 (including the primary sensor assigned to the module and supplementary sensors) are communicated to the on-body module 12, which works as a master in the system. The supplementary sensors may be realized in the form of flexible patches comprising flexible electronics. The acquired data from may be communicated to a remote device 16, preferably by a bluetooth low energy (BLE) connection, via the master.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

What is claimed is:

1. A medical sensor system, comprising:
   a sensor configured to be implanted under the skin of a user;
   an on-body module configured for attachment to the skin in the region of the implantable sensor; and
   the on-body module having a self-adhering flexible electronics patch including a first transmitter operable to exchange data with the implantable sensor via a short-range wireless connection, wherein the data exchange is based on near-field communication (NFC) protocol;
   wherein the flexible electronics patch has flexible printed circuits provided on an insulating foil substrate and the length or width of the entire self-adhering flexible electronics patch is stretchable in at least one direction by more than 20% of its initial length.

2. The medical system according to claim 1, wherein the insulating foil substrate has a thickness in the range of 10-250 microns.

3. The medical system according to claim 1, wherein the insulating foil substrate has a thickness in the range of 50-100 microns.

4. The medical system of claim 1, wherein the flexible printed circuits include at least one of conductive paths, resistors, capacitors and batteries as deformable components.

5. The medical system according to claim 1, wherein the flexible electronics patch comprises at least one of integrated circuit chips, processors, storage media, antennas and batteries as rigid or semi-rigid components distributed such that the electronics patch remains deformable.

6. The medical system according to claim 1, further comprising a pair of antennas coupleable by electromagnetic induction and configured to establish the short-range wireless connection.

7. The medical system according to claim 1, wherein the first transmitter is operable to receive measured values from the sensor and to transmit calibration data to the sensor.

8. The medical system according to claim 1, wherein the on-body module further comprises a patch-mounted energy supply configured to supply the sensor with energy by contactless transmission.

9. The medical system according to claim 1, wherein the on-body module further comprises a second transmitter integrated with the patch and operable for wireless data exchange with an external data acquisition device positioned in a far-field region.

10. The medical system according to claim 1, further comprising a body-mounted pump to deliver doses of a medical agent to the body of the user in response to a measuring result achieved with the sensor.

11. The medical system according to claim 1, wherein the on-body module comprises at least one of a controller, switches, and a display directly attached to the flexible patch for allowing the user to operate the system without remote control.

12. The medical system according to claim 1, wherein the sensor comprises a plurality of sensors distributed in a body area and connected in a network to the on-body module, wherein the plurality of sensors are adapted to measure at least one parameter selected from the group consisting of glucose, temperature, body movement, tremor, heart rate, and perspiration.

13. The medical system according to claim 1, wherein the sensor is a glucose sensor.

14. A method for continuous monitoring of at least one analyte in at least one body fluid using the medical system according to claim 1, the method comprising:
  i) using the self-adhering flexible electronics patch to attach the on-body module to the skin of a user in the region of the sensor implanted under the skin of the user; and
  ii) exchanging data between the first transmitter of the self-adhering flexible electronics patch with the implantable sensor via a short-range wireless connection.

15. The medical system according to claim 1, further comprising a battery disposed on the insulating foil substrate.

16. The medical system according to claim 15, wherein the battery is formed of functional material printed on a flexible substrate.

17. The medical system according to claim 1, wherein the substrate has sufficient unoccupied space such that the self-adhering flexible electronics patch is stretchable in at least one direction by more than 20%.

18. The medical system according to claim 1, wherein the length or width of the entire patch may be increased by at least 20% by stretching.

* * * * *